United States Patent [19]
Strauss, III

[11] Patent Number: 6,140,099
[45] Date of Patent: Oct. 31, 2000

[54] METHOD OF DELAYING FETAL MEMBRANE RUPTURE BY INHIBITING MATRIX METALLOPROTEINASE-9 ACTIVITY

[75] Inventor: Jerome Strauss, III, Wyndmoor, Pa.

[73] Assignee: The Trustees of the University of Pennsylvania, Philadelphia, Pa.

[21] Appl. No.: 08/993,900

[22] Filed: Dec. 18, 1997

Related U.S. Application Data

[60] Continuation-in-part of application No. 08/727,883, Oct. 9, 1996, Pat. No. 5,698,404, which is a division of application No. 08/246,814, May 20, 1994, Pat. No. 5,641,636.

[51] Int. Cl.$^7$ .............................. C12N 9/50; G01N 33/48; G01N 33/00; A01N 37/12
[52] U.S. Cl. .......................... 435/219; 435/267; 436/65; 436/120; 436/131; 514/2; 514/12; 514/21; 514/563; 514/575
[58] Field of Search ................................... 514/2, 12, 21, 514/563, 575; 424/94.67; 435/18, 23, 24, 219, 267, 262, 963; 436/65, 119, 120, 131

[56] References Cited

U.S. PATENT DOCUMENTS

| | | |
|---|---|---|
| 4,235,885 | 11/1980 | Sundeen et al. . |
| 4,263,293 | 4/1981 | Sundeen et al. . |
| 4,276,284 | 6/1981 | Brown . |
| 4,297,275 | 10/1981 | Sundeen et al. . |
| 4,367,233 | 1/1983 | Clark et al . |
| 4,371,465 | 2/1983 | McGregor . |
| 4,371,466 | 2/1983 | McGregor . |
| 4,374,765 | 2/1983 | McGregor . |
| 4,376,110 | 3/1983 | David et al. . |
| 4,382,081 | 5/1983 | Sundeen et al. . |
| 4,558,034 | 12/1985 | Galardy et al. . |
| 4,704,383 | 11/1987 | McNamara et al. . |
| 4,992,537 | 2/1991 | Goldberg . |
| 5,698,404 | 12/1997 | Strauss, III et al. ...................... 435/74 |

FOREIGN PATENT DOCUMENTS

| | | |
|---|---|---|
| WO 90/05719 | 5/1990 | WIPO . |
| WO93/23075 | 11/1993 | WIPO . |
| WO 94/09825 | 5/1994 | WIPO . |

OTHER PUBLICATIONS

Lehtovirta et al., 1994, Biochimica et Biophysica Acta 1206:83–89.
Osmers et al., 1990, Arch. Gynecol. Obstet. 248:75–80.
Rajabi et al., 1988, Am. J. Obstet. & Gyn. 159:971–976.
Al–Zaid et al., 1980, Br. J. Obstet. Gynecol. 87:227–229.
Andersson et al., 1989, J. Biol. Chem. 264:8222–8229.
Barrett et al., 1973, Biochem. J. 133:709–724.
Bickett et al., 1993, Anal. Biochem. 212(1):58–64.
Boone et al. 1990, Proc. Natl. Acad. Sci. USA 87:2800–2804.
Creasy, 1991, New Engl. J. Med. 325(10):727–728.
Creasy et al., 1990, Obstet, Gynecol. 76:Suppl: 2S–4S.
DeClerk et al. 1989, J. Biol. Chem. 264:17445–17453.
Evaldson et al., 1987, Gynecol. Obstet. Invest. 24:92–94.
Fernandez et al. 1992, Lab. Invest. 66:572–579.
Goldberg et al., 1992, J. Biol. Chem., vol. 267:4583–4591.
Hibbs et al., 1985, J. Biol. Chem. 260:2493–2500.
Johnson et al., 1993, Drugs, No. 5, vol. 45:684–692.
Katsura et al., 1989, FEBS Letters 244(2):315–318.
Kelly et al., 1992, The Lancet, vol. 339:776–777.
Laemmli, 1970, Nature 227:680–684.
Landolfi, 1991 J. Immunol. 146(3):915–919.
Lei et al., 1997, J. Clin. Invest. 98:1971–1978.
Lockwood et al., 1991, New Engl. J. Med. 325(10):669–674.
MacLennan et al., 1990, Lancet 15 335:267–269.
Main et al., 1985, Am. J. Obstet. Gynecol. 151:892–898.
Malak et al., 1994, Br. J. Obstet. 101:375–386.
Manicourt et al., 1993, Anal. Biochem. 215(2):171–179.
Matsuura et al., 1985, Proc. Natl. Acad. Sci. USA 82:6517–6521.
McCormick, "Trends in Rates of Low Birthweight in the United States," In Berendes HW, Kessel S, Yaffe S, (eds.) Advances In the Prevention of Low Birthweight, Washington, D.C.: National Center for Education in Maternal and Child Health, 1991:3–11.
McCormick, 1985, New Engl. J. Med. 312:82–90.
Moll et al., 1990, Cancer Res. 50:6162–7.
Morodomi et al., 1992, Biochem J. 285:603:611.
Okada et al., 1992, J. Biol. Chem. 267(30):21712–21719.
Ramos–DeSimone et al., 1993, Hybridoma 12(41):349–363.
Romero et al., May 1993, Contemp. OB/GYN:33–44.
Rush et al., 1976 Brit. Med. J. 2:965–958.
Skinner et al., 1981, Obstet. Gynecol. 57:487–489.
So et al., 1993, Acta. Obst. Gynaec. (Jpn) 45(3):227–233.
So et al., 1992, Biol. Reprod. 46:772–778.
Sunada et al., 1980, J. Biochem 87:1765–1771.
Towbin et al., 1979, Proc. Natl. Acad. Sci. USA 76(9):4350–4354.
Vadillo–Oretega, et al., 1995, Am. J. Path., vol. 146:148–156.
Vadillo–Oretega, et al., 1991, Am. J. Obstet. Gynecol. (2) 164:664–668.
Vadillo–Oretega, 1990, Obstet. Gynecol. 75:84–88.
Wilhelm et al., 1989, J. Biol. Chem. 264(20):17213–17221.
Woessner, 1991, FASEB J. 5:2145–2154.

*Primary Examiner*—Keith D. MacMillan
*Assistant Examiner*—P. Ponnaluri
*Attorney, Agent, or Firm*—Akin, Gump, Strauss, Hauer & Feld, L.L.P.

[57] ABSTRACT

The invention relates to compositions and methods for delaying the onset of fetal membrane rupture in a human. The method comprises administering to the human a metalloproteinase-9 inhibitor in an amount effective to delay the onset of fetal membrane rupture in the human.

8 Claims, 8 Drawing Sheets

FIG. 6A  FIG. 6B

METHOD OF DELAYING FETAL MEMBRANE RUPTURE BY INHIBITING MATRIX METALLOPROTEINASE-9 ACTIVITY

CROSS REFERENCE TO RELATED APPLICATIONS

This application is a continuation-in-part of U.S. application Ser. No. 08/727,883, filed on Oct. 9, 1996, issued as U.S. Pat. No. 5,698,404, which is a divisional of U.S. application Ser. No. 08/246,814, issued U.S. Pat. No. 5,641,636.

GOVERNMENT SUPPORT

This invention was supported in part by a grant from the U.S. Government (National Institutes of Health Grant No. HD34226) and the U.S. Government may therefore have certain rights in the invention.

FIELD OF THE INVENTION

The invention relates to the field of obstetrics and gynecology, and particularly to the biochemistry surrounding the phenomenon of fetal membrane rupture.

BACKGROUND OF THE INVENTION

Premature or preterm delivery of otherwise normal babies is a problem throughout the world, in both developed and developing countries. In fact, delivery of infants before the completion of 37 weeks of gestation is the leading cause of neonatal morbidity and mortality in the United States, (McCormick, 1985, New Engl. J. Med. 312:82–90), where the incidence of such deliveries has hovered around 7–9% for many years (McCormack, "Trends in Rates of Low Birthweight in the United States," In Berendes HW, Kessel S, Yaffe S, (eds.) Advances In The Prevention Of Low Birthweight, Washington, D.C.: National Center for Education in Maternal and Child Health, 3–11). Studies have shown that preterm, neonates account for more than half, and perhaps as much as 75%, of the mortality and morbidity among newborns who do not have congenital abnormalities (Rush et al., 1976, Brit. Med. J. 2:965–958). Although various intervention programs have claimed success in reducing the number of preterm deliveries, the results of these studies have been difficult to reproduce or sustain (Creasy et al., 1990, Obstet. Gynecol. 76:Suppl: 2S–4S). Thus, as perinatal mortality and morbidity stemming from other causes have decreased, the relative magnitude of the problem of preterm delivery has increased, despite significant improvements in neonatal care (Creasy, 1991, New Engl. J. Med. 325(10):727–728).

The medical profession has acknowledged that preventing preterm labor or rupture of fetal membranes is far more desirable than dealing with the problem after the fact. A solution to the problem has been exacerbated because preterm birth is a multifaceted event having different causes. Most of the current approaches to the prevention of preterm birth rely in part on risk-scoring systems to identify a group of women to whom special attention can be directed. These rely on such factors as obstetrical history, demographic factors, and premonitory symptoms (Main et al., 1985, Am. J. Obstet. Gynecol. 151:892–898). However, these approaches have been roundly criticized as being neither sensitive nor specific. For example, application of these methods to multiple pregnancies, including bed rest in pregnancies with twins, has been shown to be of little value (MacLennan et al., 1990, Lancet 15 335:267–269). Current treatment regimens have also been frequently hampered by an advance stage of labor or the inability to distinguish between irrelevant contractions and true preterm labor (Lockwood et al., 1991, New Engl. J. Med. 325(10):669–674). Thus, effective preventative measures have been essentially unavailable, largely because of the inability to predict the problem with enough certainty to warrant enrolling patients in a trial of preventative approaches (Creasy et al., supra).

A majority of research has focused on identifying a biochemical marker predictive of spontaneous preterm labor or premature rupture of the fetal membranes. Various candidates for biochemical markers of preterm delivery, e.g., plasma estradiol-17 beta, progesterone, and C-reactive protein, have not withstood rigorous scrutiny (Lockwood, supra). Lockwood et al. studied fetal fibronectin as a marker candidate, based upon the previous identification of this ubiquitous plasma and extracellular matrix protein in amniotic fluid and placental tissue (Matsuuia et al., 1985, Proc. Natl. Acad. Sci. USA 82:6517–6521). The hypothesis put forth by Lockwood et al. centers on the fact that mechanical or inflammatory-mediated damage to the fetal membrane before preterm delivery results in the release of fibronectin into the cervix and vagina. However, these authors recognized that this test was not as accurate predictor of preterm delivery. In addition, others (Creasy et al., 1990, Obstet. Gynecol. 76:Suppl: 2S–4S) supported the fact that the presence of fetal fibronectin was not indicative of premature fetal membrane rupture.

The chorioamniotic membranes are essentially connective tissue structures. Since collagen determines the tensile strength of fibrous connective tissue, there has been considerable interest in investigating collagen biochemistry in the setting of premature fetal membrane rupture (Romero et al., May 1993, Contemp. OB/GYN:33–44). Some investigators have detected low collagen content in membranes that have ruptured prematurely as compared with normal membranes, and suggested that the tensile property of the amniotic membranes which rupture must be lower than the tensile property in normal membranes (Skinner, et al., 1981, Obstet. Gynecol. 57:487–489). However, other groups have found no difference in the connective tissue collagen content in prematurely ruptured fetal membranes (Al-Zaid et al., 1980, Br. J. Obstet. Gynecol. 87:227–229; Evaldson et al., 1987, Gynecol. Obstet. Invest. 29:92–94). There have been yet other reports of high levels of collagenolytic activity in prematurely ruptured fetal membranes and in the serum of women with preterm labor (Vadillo-Oretega, 1990, Obstet. Gynecol. 75:84–88). However, the precise mechanism underlying these biochemical changes has remained unknown (Katsura et al., 1989, FEBS Letters 244 (2):315–318); So et al., 1992, Biol. Reprod. 46:772–78). Enzymes capable of degrading collagen have been previously described as products of cultured cells derived from fetal membranes (So et al., 1993, Acta. Obst. Gynaec. (Jpn) 45(3):227–233).

The immunocytochemical detection of collagenase (MMP-2) in fetal membranes was reported in Fernandez et al. (1992, Lab. Invest. 66:572–579). The enzyme family known as matrix metalloproteinases (MMPs) has been implicated in many normal tissue remodeling processes such embryonic development, postpartum involution of the uterus, bone and growth plate remodeling, ovulation, and wound healing, as well as pathological conditions such as arthritis, tumor invasion and metastasis (Woessner, 1991, FASEB J. 5:2145–2154.) While these enzymes may act on certain common substrates such as denatured collagen (gelatin) in vitro, they undoubtedly have specific natural substrates in vivo which account for their distinct roles in specific cellular processes. The enzymes described by So et al. (supra), namely MMP-1 and MMP-3, have not been correlated with structural changes in fetal membranes.

Despite the advances which have been made in understanding fetal development and in managing prenatal care, there remains a long felt need in the art for a specific and reliable biochemical marker with which to predict premature fetal membrane rupture. The identification of a marker of premature fetal membrane rupture would serve as a means of identifying and developing compositions capable of delaying premature fetal membrane rupture for which there is also a long felt need.

SUMMARY OF THE INVENTION

The invention relates to a method of delaying the onset of fetal membrane rupture in a human. The method comprises administering to the human a metalloproteinase-9 inhibitor in an amount effective to delay the onset of fetal membrane rupture in the human.

In one embodiment, the metalloproteinase-9 inhibitor is a hydroxamic acid-based compound having the formula:

wherein $R^1$ represents a $C_1-C_6$ alkyl, phenyl, thiophenyl, substituted phenyl, phenyl ($C_1-C_6$) alkyl, heterocycyl, ($C_1-C_6$) alkylcarbonyl, phenacyl or substituted phenacyl group; or, when n=o, $R^1$ represents $SR^x$,
wherein
$R^x$ represents a group wherein $R^2$ represents a hydrogen atom or a $C_1-C_6$ alkyl, $C_1-C_6$ alkenyl, phenyl ($C_1-C_6$) alkyl, cycloalkyl ($C_1-C_6$) alkyl or cycloalkenyl ($C_1-C_6$) alkyl group;

$R^3$ represents an amino acid side chain or a $C_1-C_6$ alkyl, benzyl, ($C_1-C_6$ alkoxy) benzyl, benzyloxy ($C_1-C_6$ alkyl) or benzyloxybenzyl group;

$R^4$ represents a hydrogen atom or a $C_1-C_6$ alkyl group;

$R^5$ represents a hydrogen atom or a methyl group;

n is an integer having the value 0, 1 or 2; and

A represents a $C_1-C_6$ hydrocarbon chain optionally substituted with one or more $C_1-C_6$ alkyl, phenyl or substituted phenyl groups;

or a salt thereof.

In a preferred embodiment, the metalloproteinase-9 inhibitor is batimastat.

Preferably, the metalloproteinase-9 inhibitor is suspended in a pharmaceutically acceptable carrier.

In another embodiment, the metalloproteinase-9 inhibitor is administered to the human by a route selected from the group consisting of intra-amniotic, vaginal and parenterally.

In yet another embodiment, the metalloproteinase-9 inhibitor is administered to the human in a dosage of from at least about 0.1 mg/kg of body weight per day to about 300 mg/kg of body weight per day. In one aspect, the dosage is from at least about 1 mg/kg of body weight per day to about 250 mg/kg of body weight per day. In another aspect, the dosage is from at least about 25 mg/kg body weight per day to about 250 mg/kg of body weight per day.

There is also included in the invention a method of inducing labor in a human comprising administering to the human a metalloproteinase-9 activator in an amount effective to induce fetal membrane rupture, thereby inducing labor.

In one embodiment, the metalloproteinase-9 activator is selected from the group consisting of a cytokine, a chemical agent, a growth factor, a prostanoid, a phorbol myristal ester and trypsin. When the metalloproteinase-9 activator is a cytokine, the cytokine is selected from the group consisting of interleukin-1α and tumor necrosis factor α.

In another embodiment, the metalloproteinase-9 activator is 4-aminophenylnercuric acetate.

The invention further relates to a method of inducing labor in a human comprising administering to the human metalloproteinase-9 in an amount effective to induce fetal membrane rupture, thereby inducing labor.

BRIEF DESCRIPTION OF THE FIGURES

FIG. 4A comprising FIGS. 4A-1 through 4A-4 is an image of a zymogram depicting MMP-13 activity. FIGS. 4A-1 through 4A-4 are zymograms of chicken fetal membranes incubated in the absence FIG. 4A-1 or presence FIG. 4A-2 of EDTA. FIGS. 4A-3 and 4A-4 are zymograms of amniotic fluid incubated in the absence FIG. 4A-3 or presence FIG. 4A-4 of EDTA.

FIG. 6 comprising

DETAILED DESCRIPTION

Applicants' invention is predicated upon their unexpected and surprising discovery that metalloproteinase-9 ("MMP-9"), and particularly its active species, are present in human fetal membranes, particularly the amnion epithelium, fibroblasts, and chorion laeve trophoblast cells, only during labor or after delivery. Specifically, active MMP-9 was detected in these tissue extracts of fetal membranes collected from women in active labor and after delivery. In contrast, however, substantially no MMP-9 activity was detected in membranes removed prior to the onset of labor. On the basis of these findings, and while not intending to be bound by any particular theory, Applicants believe that activation of MMP-9 results in the degradation of collagenous matrix of the fetal membranes, and thus facilitates their rupture under both normal physiological and pathological conditions.

According to the present invention, a tissue or fluid sample of fetal membrane origin obtained from a gestative female is assayed for the presence or absence of MMP-9 activity, wherein the presence of such activity is a positive indication of the onset of fetal membrane rupture. The reliability and accuracy of the method is dependent upon the sample being necessarily of fetal membrane origin. The sample may be a tissue, e.g., a biopsy of the membrane, or a fluid which is either contiguous with the membrane or otherwise interactive with the membrane in such a way that its biochemical constituency, particularly its MMP-9 concentration, is fairly representative of the state of the membrane at any given time during gestation. Examples of such fluids include cervicovaginal fluids, e.g., cervical fluid or vaginal fluid, plasma and serum. Cervical fluid is preferred. Fluid samples, which are preferred, may be conveniently obtained using a swab or any other suitable collection device. The thus-obtained fluid sample is then placed in a predetermined volume of extraction medium, e.g., SDS-PAGE sample buffer, that serves to remove proteins from the collection device. This medium is used as the test material for the detection of MMP-9 activity. Alternatively, the MMP-9 activity may be assayed directly on the sample while it remains in the device.

MMP-9, also known as the 92-kDa type IV collagenase/gelatinase or gelatinase B protein, is the largest member of this metalloproteinase enzyme family. The purification of MMP-9 and the cDNA sequence encoding this enzyme are disclosed in U.S. Pat. No. 4,992,537 (Goldberg et al.). The zymogen form of MMP-9, i.e., proMMP-9, is initially activated to produce an intermediate active form of the enzyme of about $M_r$ 83 kDa and a 9 kDa inactive proteolytic cleavage fragment. The 83 kDa is then further proteolytically processed to yield an active species of enzyme of about $M_r$ 67 kDa and a 16 kDa inactive proteolytic cleavage product (Okada et al., 1992, J. Biol. Chem. 267(30):21712–21719). All active species of the enzyme have the ability to bind to 2 macroglobulin. (Barrett et al., 1973, Biochem. J. 133:709–724).

By the term "MMP-9 activity," it is meant the presence of any active, e.g., gelatinolytic, species of MMP-9 such as the intermediate 83 kDa species and the 67 kDa species, which are the two most prominent catalytically active species of MMP-9. Since the presence of the 9 and 16 kDa inactive proteolytic cleavage products of MMP-9 are indicative of the presence of active MMP-9 they are therefore included in the definition of "MMP-9 activity," as used herein.

The assay for the detection of MMP-9 activity may be performed in accordance with a variety of art-recognized procedures. For example, quantitative zymographic methods provide a relatively refined assessment of the activity of this enzyme. These methods facilitate the detection of MMP-9 activity based upon the ability of the enzyme to hydrolyze denatured collagen, i.e., gelatin, which is a natural substrate for MMP-9. Hydrolyzed gelatin is incorporated into a gel such as polyacrylamide and is readily detected therein (Hibbs et al., 1985, J. Biol. Chem. 260:2493–2500; Moll et al., 1990, Cancer Res. 50:6162–70).

A zymographic assay may be standardized using known concentrations of a purified MMP-9 preparation that is analyzed in parallel with the test sample. Purified MMP-9 may be prepared using methods known in the art (Okada et al., supra.; Morodomi et al., 1992, Biochem J. 285:603:611). The extent of hydrolysis of gelatin in the assay is directly related to the activity of MMP-9 in the sample.

Active forms of MMP-9 can be identified by their characteristic molecular weights. During gelatin zymography, the proMMP-9 species can be detected because of the catalytic activation that occurs during electrophoresis and subsequent incubation. However, the MMP-9 forms which are present prior to the onset of labor are incapable of undergoing this kind of activation, i.e., they are latent.

MMP-9 activity may also be detected using standard immunological techniques, such as, but not limited to, ELISA, immunofluorescence assays, and radioimmunoassays. In a preferred embodiment, MMP-9 activity is detected using an ELISA, which entails the use of antibodies specific for MMP-9 (David et al, U.S. Pat. No. 4,376,110 and references cited therein). Monoclonal antibodies specific for MMP-9 have been prepared using partially purified enzyme preparations (Moll et al., 1993, supra; Ramos-DeSimone et al., 1993, Hybridoma 12(41):349–363; Goldberg et al., supra). Polyclonal antibodies specific for MMP-9 may also be prepared in animals in accordance with standard procedures. In a preferred embodiment, polyclonal antibodies are prepared against non-conserved peptides of MMP-9 which are conjugated to a macromolecular carrier. The isolation of a specific non-conserved peptide of MMP-9 such as the metal-binding domain, is considered within the level of ordinary skill in the art (Woessner, and Goldberg et al., supra). Enzymic assays which facilitate detecting MMP-9 in picogram or nanogram amounts are also disclosed in Manicourt et al., (1993, Anal. Biochem. 215(2):171–179).

MMP-9 activity may also be detected in a sample using western blot analysis, which requires electrophoretic separation of the test material in a gel, followed by transfer of the separated proteins to a nitrocellulose membrane. Detection of the MMP-9 antigens is accomplished using a specific antibody and a reagent that reacts with the antigen-antibody complex (Towbin et al., 1979, Proc. Natl. Acad. Sci. USA 76(9):4350–4354).

In the cases where MMP-9 activity is assessed by assaying for the presence of the inactive proteolytic cleavage products, such detection must be performed immunologically using antibodies specific for these products.

As mentioned above, an MMP-9 detection reagent may be fixed to the collection device, whereupon the detection of MMP-9 activity is accomplished by exposing the collection device to a detectably labeled reagent specific for the enzyme, followed by development of a visual signal, e.g., an enzyme-based color reagent, which indicates the presence of active MMP-9. This assay methodology is currently employed in urinary pregnancy tests and ovulation prediction tests.

While the detection of MMP-9 activity in many cases may be taken as a positive indication of the onset of fetal membrane rupture, the reliability of the method may be enhanced by quantifying the MMP-9 activity in the sample and then comparing the level of MMP-9 activity with an established control level of MMP-9 activity, e.g., the average levels which are identified in a prospective longitudinal analysis of normal specimens collected from women who delivered at term. This level is referred to herein as a "control level." One skilled in the art would necessarily expect that this control level would be substantially negligible in view of the present observation that MMP-9 exists in a latent inactive form prior to labor. In other words, any detectable non-negligible (control) MMP-9 activity should be taken to be predictive of the onset of labor. Since labor may occur within a matter of days or even hours following detection of MMP-9 activity, close monitoring of the patient should be initiated immediately following detection of any level of MMP-9 activity which exceeds the control level. MMP-9 containing samples should then be obtained from the at-risk patient periodically, e.g., daily or even more frequently, to generate a time course analysis of the expression of active MMP-9. Therapeutic or other intervention may then be initiated as deemed necessary.

In view of the working hypothesis that the underlying biochemical mechanisms surrounding fetal membrane rupture are substantially identical in both normal and pathological conditions, the method of the present invention is equally predictive of the onset of term labor in addition to as pre-term labor.

By the term "term labor," as used herein, is meant labor which occurs at the end of a normal gestation period, i.e., at about week 37. By the term "pre-term labor" as used herein, refers to the onset of labor any time therebefore, and the term "post-term" labor is used herein to refer to the onset of labor thereafter.

Thus, the method of the present invention is advantageously practiced to identify patients at risk of premature membrane rupture, as well as to monitor patients already suspected of being at risk, e.g., those having a predisposition to fetal membrane rupture having a history of delivery of twins, or having a history of drug or alcohol abuse, diabetes or hypertension. In these cases, the method of present invention may be employed beginning during the second trimester of pregnancy, e.g., at about the 22nd or 23rd week, and be performed periodically (e.g., daily, weekly, or more or less frequently) thereafter, depending on such factors as the results of the previous assay. The method is further effectively practiced on ostensibly low risk patients to investigate any sudden cervical changes, or simply as a routine measure during the last trimester of pregnancy to provide a more accurate prediction of the delivery date.

In another embodiment of the present invention, an MMP-9 inhibitor is administered to a gestative female, particularly one suspected of being at imminent risk of fetal membrane rupture, in order to delay such membrane rupture. By the term "MMP-9 inhibitor" as used herein, is meant any natural or synthetic substance capable of rendering active MMP-9 catalytically inactive or of rendering proMMP-9 incapable of being proteolytically processed to its active forms, or of rendering endogenous activators of MMP-9 inactive.

Several inhibitors of MMP-9 are known in the art. These include, for example, a 29 kDa tissue inhibitor of metalloproteinase-1 ("TIMP-1") (Moll et al., supra), 1,10-phenanthroline, and monoclonal antibodies specific for MMP-9 (Ramos-DeSimone, supra). The cDNA sequence of TIMP-1 is disclosed in Boone et al. (1990, Proc. Natl. Acad. Sci. USA 87:2800–2804. The purification of TIMP-1 is disclosed in DeClerk et al. (1989, J. Biol. Chem. 264:17445–17453. Various chelating agents, e.g., EDTA (ethylene diamine tetraacetic acid) bis-(dioxopiperazine)s, particularly 2,6-dioxopiperazines, also have been found to inhibit type IV collagenases in vivo. See W.O. 9323075 (PCT/US93/04542) (Liang et al.), and the references cited therein, including the collagenase inhibitors disclosed in U.S. Pat. Nos. 4,367,233; 4,371,465; 4,371,466; 4,374,765; 4,235,885; 4,263,293; 4,297,275; 4,382,081; 4,558,034; 4,276,284; and 4,704,383. Other inhibitors of MMP-9 include enzymes such as proteases which provide for the inactivation of MMP-9 by cleaving it into inactive fragments. Also included are antisense RNAs which inhibit expression of MMP-9 activity. Those skilled in the art may determine other therapeutically effective inhibitors of MMP-9 in accordance with standard screening assays (Bickett et al., 1993, Anal. Biochem. 212(1):58–64, and Liang et al. supra. The inhibitor TIMP-1, for example, may be modified to produce an analog conjugate or derivative for the purpose of increasing both potency and half-life of this compound. One means of accomplishing this is to prepare a complex of this inhibitor with an IgG molecule having a disarmed effector function. (Landolphi, 1991 J. Immunol.146(3):915–919).

An MMP-9 inhibitor is administered to a patient in an amount effective to delay fetal membrane rupture, which in turn delays the onset of labor. From a clinical point of view, it is especially advantageous to delay the onset of labor until at least 30 weeks, and preferably until at least 34 weeks of gestation. This allows the fetus to mature, and thus increase the chances of survival of the same. The dosage amount and mode of administration of any given inhibitor depends on several factors including the chemical nature of the inhibitor and the seriousness of the condition. In general, an effective amount of the inhibitor which is administered to the patient will range from at least 0.01 mg/kg of body weight per day to about 1000 mg/kg of body weight per day. Those skilled in the art are able to determine preferred dosage amounts using suitable experimental models such as subhuman primates (e.g., baboon).

An MMP-9 inhibitor may be administered in any pharmaceutically acceptable formulation. In addition, the route of administration may vary depending upon such factors as the severity of the condition and the age and overall health of the fetus and the mother. Typically the inhibitor is administer orally or parenterally. However intra-amniotic or parenteral delivery and vaginal suppositories are preferred. Of course, those skilled in the art will appreciate that the rate of the administration of the MMP-9 inhibitor can be achieved by the use of sustained-release drug delivery systems known in the art as discussed herein.

In a preferred embodiment of this aspect of the present invention, the MMP-9 inhibitor is a hydroxamic acid based compound represented by formula (I), as follows:

wherein:

$R^1$ represents a $C_1$–$C_6$ alkyl, phenyl, thiophenyl, substituted phenyl, phenyl ($C_1$–$C_6$) alkyl, heterocyclyl, ($C_1$–$C_6$)

alkylcarbonyl, phenacyl or substituted phenacyl group; or, when n=o, $R^1$ represents $SR^x$, wherein $R^x$ represents a group:

$R^2$ represents a hydrogen atom or a $C_1$–$C_6$ alkyl, $C_1$–$C_6$ alkenyl, phenyl ($C_1$–$C_6$) alkyl, cycloalkyl ($C_1$–$C_6$) alkyl or cycloalkenyl ($C_1$–$C_6$) alkyl group;

$R^3$ represents an amino acid side chain or a $C_1$–$C_6$ alkyl, benzyl, ($C_1$–$C_6$ alkoxy) benzyl, benzyloxy ($C_1$–$C_6$ alkyl) or benzyloxybenzyl group;

$R^4$ represents a hydrogen atom or a $C_1$–$C_6$ alkyl group;

$R^5$ represents a hydrogen atom or a methyl group;

n is an integer having the value 0, 1 or 2; and

A represents a $C_1$–$C_6$ hydrocarbon chain optionally substituted with one or more $C_1$–$C_6$ alkyl, phenyl or substituted phenyl groups;

or a salt thereof.

The term "compound" includes "salt" unless the context requires otherwise.

The term "$C_1$–$C_6$ alkyl" refers to a straight or branched chain alkyl moiety having from one to six carbon atoms, including for example, methyl, ethyl, propyl, isopropyl, butyl, t-butyl, pentyl, and hexyl, and cognate terms (such as "$C_1$–$C_6$ alkoxy") are to be construed accordingly.

The term "$C_1$–$C_6$ alkenyl" refers to a straight or branched chain alkyl moiety having one to six carbons and having in addition one double bond, of either E or Z stereochemistry where applicable. This term includes, for example, an alpha, beta-unsaturated methylene group, vinyl, 1-propenyl, 1- and 2-butenyl and 2-methyl-2-propenyl.

The term "cycloalkyl" refers to a saturated alicyclic moiety having from 3 to 8 carbon atoms and includes for example, cyclopropyl, cyclobutyl, cyclopentyl and cyclohexyl.

The term "cycloalkenyl" refers to an unsaturated alicycle having from 3 to 8 carbon atoms and includes cyclopropenyl, cyclobutenyl and cyclopentenyl, cyclohexenyl.

The term "substituted," as applied to a phenyl or other aromatic ring, means the ring is substituted with up to four substituents each of which independently may be $C_1$–$C_6$ alkyl, $C_1$–$C_6$ alkoxy, hydroxy, thiol, $C_1$–$C_6$ alkylthiol, amino, halo (including fluoro, chloro, bromo and iodo), triflouromethyl or nitro.

The term "amino acid side chain" means a characteristic side chain attached to the —CH(NH$_2$) (COOH) moiety in the following R or S amino acids: glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid.

The term "hydrocarbon chain" includes alkylene, alkenylene and alkynylene chains of from 1 to 6 carbon atoms. Preferably the carbon atom of the hydrocarbon chain nearest to the hydroxamic acid group is a methylene carbon atom.

Preferred compounds include those in which, independently or in any combination:

$R^1$ represents a hydrogen atom or a $C_1$–$C_4$ alkyl, phenyl, thiophenyl, benzyl, acetyl or benzoyl group;

$R^2$ represents a $C_3$–$C_6$ alkyl (for example isobutyl) group;

$R^3$ represents a benzyl or 4-($C_1$–$C_6$) alkoxyphenylmethyl or benzyloxybenzyl group;

$R^4$ represents a $C_1$–$C_4$ alkyl (for example methyl) group; and $R^5$ represents a hydrogen atom.

More preferred compounds include:

[4-(N-Hydroxyamino)-2R-isobutyl-3S-(phenylthiomethyl)succinyl]-L-phenylalanine-N-methylamide;

[4-(N-Hydroxyamino)-2R-isobutyl-3S-(thiophenyl-thiomethyl)succinyl]-L-phenylalanine-N-methylamide (hereinafter "batimastat");

[4-(N-Hydroxyamino)-2R-isobutyl-3S-(benzylthiomethyl) succinyl]-L-phenylalanine-N-methylamide;

[4-(N-Hydroxyamino)-2R-isobutyl-3S-(acetylthiomethyl) succinyl]-L-phenylalanine-N-methylamide;

[4-(N-Hydroxyamino)-2R-isobutyl-3S-(thiolmethyl) succinyl]-L-phenylalanine-N-methylamide;

[4-(N-Hydroxyamino)-2R-isobutyl-3S-(benzoylthiomethyl) succinyl]-L-phenylalanine-N-methylamide;

[4-(N-Hydroxyamino)-2R-isobutyl-3S-(pivoaloylthiomethyl) succinyl]-L-phenylalanine-N-methyl-amide;

[4-(N-Hydroxyamino)-2R-isobutyl-3S-(phenylthiophenyl) succinyl]-L-phenylalanine-N-methyl amide sodium salt;

[4-(N-Hydroxyamino)-2R-isobutyl-3S-(4-methoxyphenyl-thiomethyl)succinyl]-L-phenylalanine-N-methylamide;

[4-(N-Hydroxyamino)-2R-isobutyl-3S-(4-hydroxyphenylthiomethyl)-succinyl]-L-phenylalanine-N-methylamide;

[4-(N-Hydroxyamino)-2R-isobutyl-3S-(2-thiophenethiomethyl)succinyl]-L-phenylalanine-N-methylamide sodium salt;

[4-(N-Hydroxyamino)-2R-isobutyl-3S-(4-methoxyphenylthiomethyl)succinyl]-L-phenylalanine-N-methylamide sodium salt;

[4-(N-Hydroxyamino)-2R-isobutyl-3S-(4-tert-butylphenylthiomethyl)succinyl]-L-phenylalanine-N-methylamide;

[4-(N-Hydroxyamino)-2R-isobutyl-3S-(2,4-dimethylphenylthiomethyl)succinyl]-L-phenylalanine-N-methylamide;

bis-S,S'-[4-(N-Hydroxyamino)-2R-isobutyl-3S-(thiomethyl) succinyl]-L-phenylalanine-N-methylamide;

[4-(N-Hydroxyamino)-2R-isobutyl-3S-(3-bromophenylthiomethyl)succinyl]-L-phenylalanine-N-methylamide;

[4-(N-Hydroxyamino)-2R-isobutyl-3S-(3-chlorophenylthiomethyl)succinyl]-L-phenylalanine-N-methylamide;

[4-(N-Hydroxyamino)-2R-isobutyl-3S-(3-methylphenylthiomethyl)succinyl]-L-phenylalanine-N-methylamide;

[4-(N-Hydroxyamino)-2R-isobutyl-3S-(4-(N-acetyl) aminophenylthiomethyl)succinyl]-L-phenylalanine-N-methylamide;

[4-(N-Hydroxyamino)-2R-isobutyl-3S-phenylsulphinylmethylsuccinyl]-L-phenylalanine-N-methylamide;

[4-(N-Hydroxyamino)-2R-isobutyl-3S-phenylsulphonylmethylsuccinyl]-L-phenylalanine-N-methylamide;

[4-(N-Hydroxyamino)-2R-isobutyl-3S-thiophenylsulphinylmethyl-succinyl]-L-phenylalanine-N-methylamide;

[4-(N-Hydroxyamino)-2R-isobutyl-3S-thiophenylsulphonylmethyl-succinyl]-L-phenylalanine-N-methylamide;

[4-(N-Hydroxyamino)-2R-isobutyl-3S-phenyl-sulphonylmethyl-succinyl]-L-phenylalanine-N-methylamide sodium salt;

[4-(N-Hydroxyamino)-2R-isobutyl-3S-(4-(isobutyloxycarbonylamino)phenyl)thiomethyl-succinyl]-L-phenylalanine-N-methylamide; and

[4-(N-Hydroxyamino)-2R-isobutyl-3S-(4-(N-methyl-N-(tert-butoxycarbonyl)-glycylamino)phenyl)thio-methylsuccinyl]-L-phenylalanine-N-methylamide.

The most preferred compound is batimastat, [4-(N-hydroxyamino)-2R-isobutyl-3S-(thiophenyl-thio-methyl)-succinyl]-L-phenylalanine-N-methylamide.

The dosage unit of the hydroxamic acid based compounds (s) of formula (I) which is orally administered to a patient may contain from about 1 to about 250 mg; preferably the unit contains from about 25 to about 250 mg. In general, a suitable daily dose may vary widely depending on the condition of the patient. However, a dose of a compound of general formula I of about 0.1 to 300 mg/kg body weight, particularly from about 40 to 100 mg/kg body weight is appropriate.

The hydorxamic acid based compounds are commercially available from British Biotech Pharmaceuticals Ltd. (Oxford, U.K.). Methods of synthesis of these compounds are described in PCT Publication No. 90/05719.

In a further embodiment of the present invention, MMP-9, e.g., MMP-9, or an MMP-9 activator is administered to a gestative female to induce fetal membrane rupture which in turn facilitates the onset of labor.

By the term "MMP-9 activator" as used herein is meant any pharmaceutically acceptable natural or synthetic substance that reacts with endogenous proMMP-9 to produce an active MMP-9 species, or which activates or otherwise stimulates expression of an endogenous activator of MMP-9. A variety of MMP-9 activators such as chemical agents, phorbol myristal esters, cytokines, growth factors, prostanoids (e.g., prostaglandin $E_2$), repressive factors, as well as other agents are known in the art (Woessner, supra). A preferred chemical agent is 4-aminophenylmercuric acetate (APMA). Other preferred activators include the cytokines such as interleukin-1α and tumor necrosis factor α. (So et al., 1992, Biol. Reprod. 46:772–778; Okada et al. supra; Liang et al., supra). Trypsin has also been disclosed as an effective activator of proMMP-9 (Morodomi, supra).

MMP-9 or an MMP-9 activator is advantageously administered to post-term patients (i.e., those for whom gestation is prolonged beyond 37 weeks), or otherwise when the patient or fetus is at risk. Alternatively, the method may be practiced as a matter of mere convenience provided of course that the fetus is fully mature. As in the case for the MMP-9 inhibitors, the determination of general and preferred dosage amounts, and the mode and frequency of administration of the MMP-9 activator or MMP-9 are considered within the level of skill in the art. Those teachings apply equally here in that the dosages and formulations which are recited for inhibitor of MMP-9 activity also apply to MMP-9 activities. Further, those skilled in the art would appreciate that MMP-9 activators or MMP-9 can be delivered to a patient in formulations designed to achieve a sustained release effect or which confer an increased half-life on the activator in accordance with the standard techniques described above.

The invention will be further described by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Fetal membranes were collected at term after normal delivery or at the time of elective cesarean section at term without labor. Whole membrane or amnion and chorion, which were manually separated, were processed for gelatin zymography and Western blot analyses as described below in Examples 1 and 2.

Example 1

Western Blot Analysis of MMP-9 in Human Term Fetal Membrane

Western blotting was carried out using 10 micrograms of protein per lane in 8% SDS-PAGE under non-reducing conditions. Transfer of protein to a Immunobilon-P membrane was accomplished by electrophoresis at 30 V for 12 h at 4° C. using methods described by Towbin et al., (supra). The monoclonal antibody 6-6B is disclosed in Ramos-DeSimone (supra). This antibody recognizes, under non-reducing conditions, both the proMMP-9 (92 kDa) and the intermediate active form of the enzyme (83 kDa). Primary antibody (1 microgram/ml) was applied to the blot overnight at 4° C. Binding of the primary antibody to antigens on the blot was detected using VectaStain ABC reagents (Vector Laboratories, Burlingame, Calif.).

Figure 1:
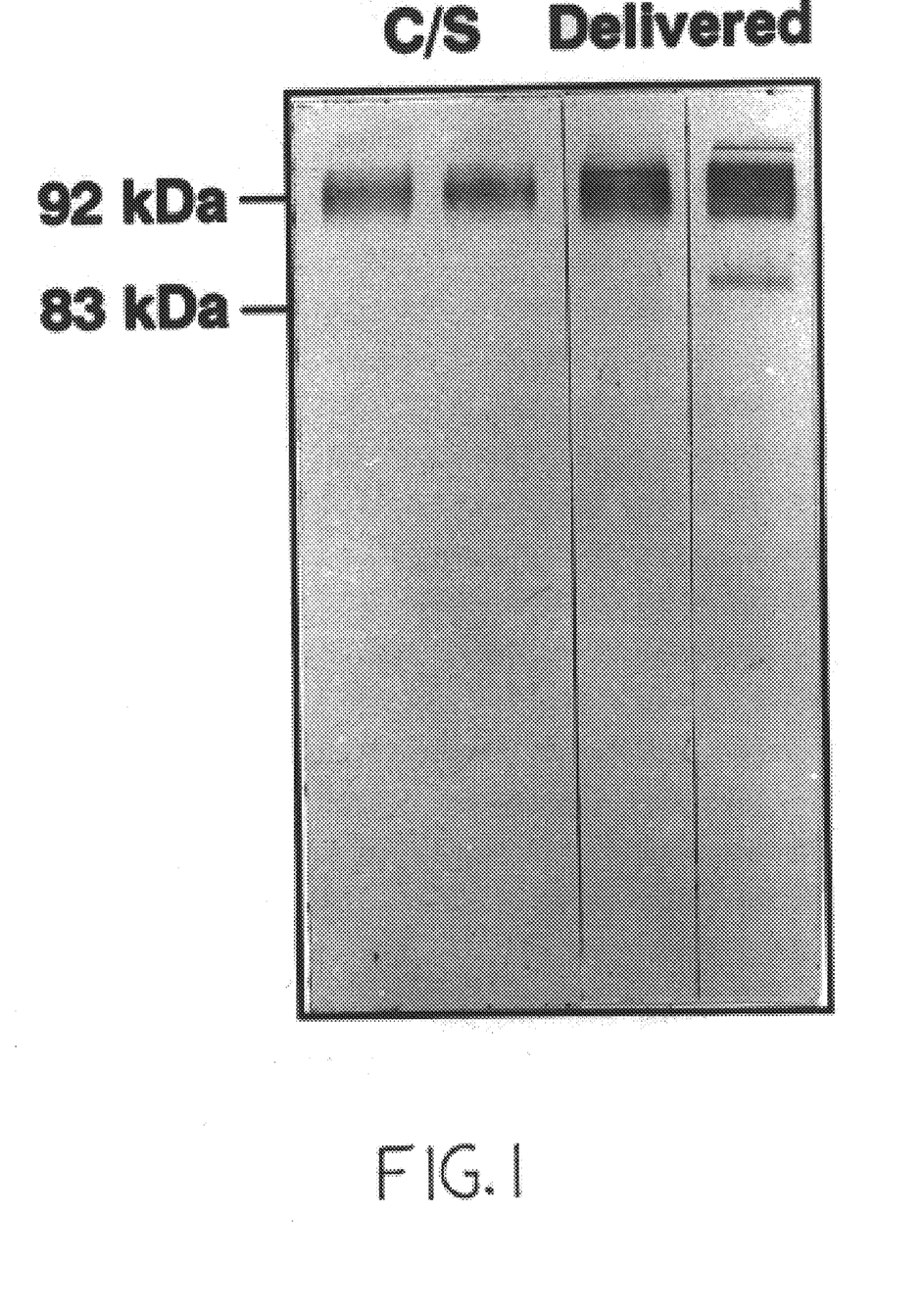
FIG. 1 is an image of a western blot depicting detection of MMP-9 in extracts of human amniochorion.

Western blot analyses revealed that MMP-9 was present in the amniochorion extracts from delivered fetal membranes as a broad band of 94–92 kDa (FIG. 1) A 83 kDa band representing the intermediate form of MMP-9 activation was observed only in specimens collected following delivery.

Example 2

Gelatin Zymographic Analysis of MMP-9 in Human Term Fetal Membranes Amnion and Chorion SDS-PAGE was performed using a mini-gel apparatus (Bio-Rad, Richmond, Calif.). Gels were prepared according to standard procedures except that pig skin gelatin (1 mg/ml) was co-polymerized in the 8% running gel and samples were added under non-denaturating conditions. Ten micrograms of protein were applied per lane and were electrophoresed under constant current (10 mA). Gels were washed in 2.5% Triton X-100 for 30 minutes and were incubated for 24 hours at 37° C. in 50 mM Tris buffer, pH 7.4, containing 0.15 M NaCl and 30 mM $CaCl_2$ or in a buffered solution to which 10 mM EDTA was added to inhibit MMP activity. Gels were stained with Coomasie R-250. Pre-stained molecular weight markers (Bio-Rad) were included in each gel.

Figure 2A:
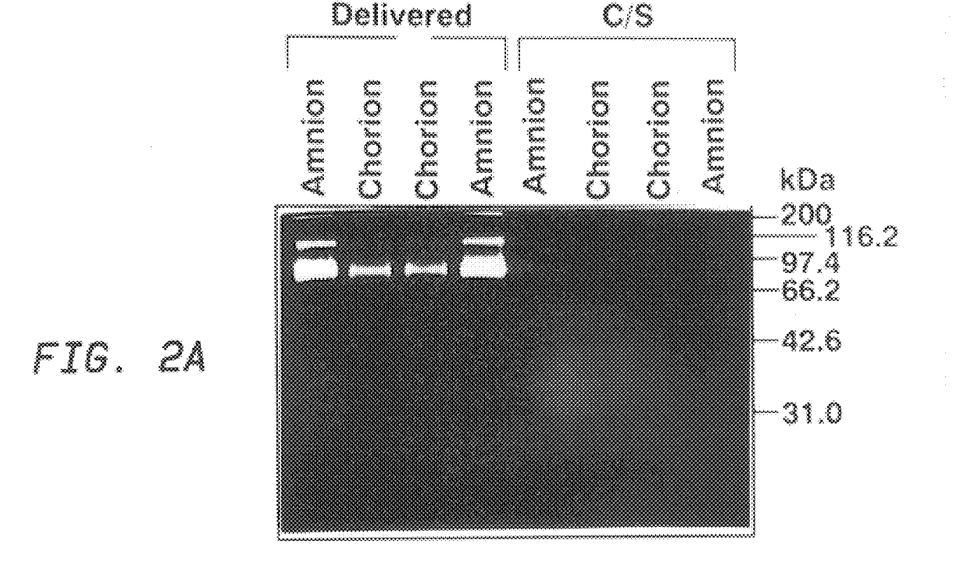
FIGS. 2A and 2B are images depicting gelatin zymographic analyses of extracts of human amnion and chorion manually separated from fetal membranes collected at cesarean section (C/S) or following delivery ("Delivered"), in the absence (FIG. 2A) or presence (FIG. 2B) of 10 mM EDTA.
Figure 2B:
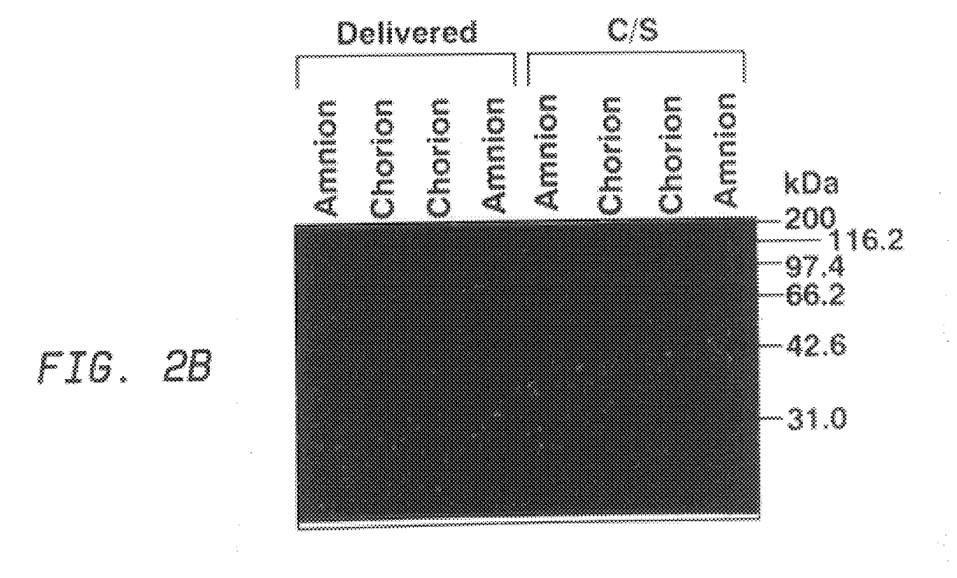

Extracts of amniochorion obtained following active labor contained five lysis bands in zymograms ranging in size from about 68 to 150 kDa with the most prominent band being a 92 kDa gelatinase. These activities were also present in separated amnion and chorion laeve, with greater activity consistently being found in amnion (FIG. 2A). Lytic activity in the amnion and chorion laeve extracts was completely inhibited in the presence of 10 mM EDTA, indicating that the gelatinases are MMPs (FIG. 2B). The molecular weights of the gelatinases suggested that MMP-9 was a primary component. Gelatin zymography detected MMP-9 dimers (150 kDa), the 92 dKa proenzyme, and activated enzyme species having molecular weights of 83 kDa and 68 kDa.

In marked contrast to the delivered membranes, extracts of amniochorion, and separated amnion and chorion laeve from women not in labor (elective cesarean section) contained negligible gelatinase activity (FIG. 2A).

Example 3

Figure 3A:
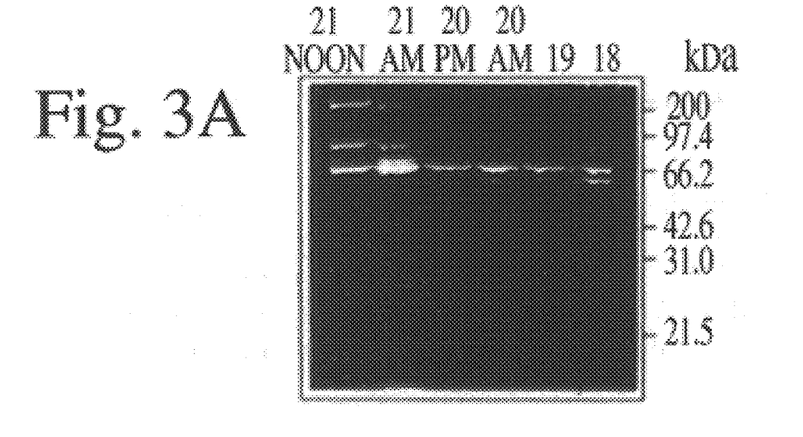
FIGS. 3A and 3B are images depicting polyacrylamide gel electrophoretic (PAGE) analyses of homogenized fetal membranes obtained from pregnant Spraque-Dawley rats killed at the indicated days of pregnancy and times during normal gestation.
Figure 3B:
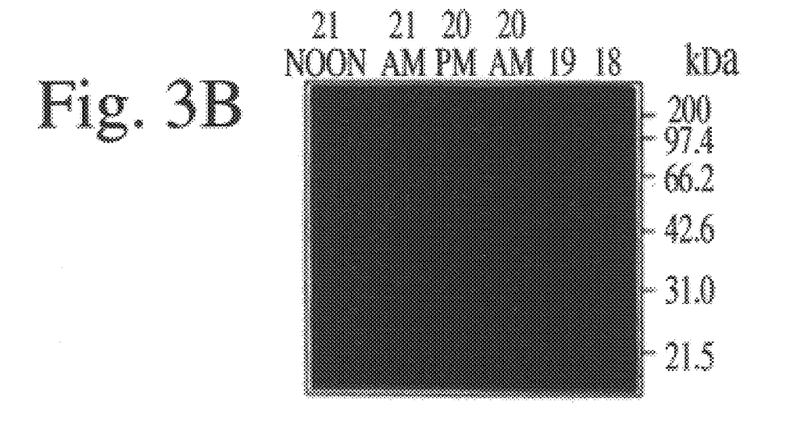
Figure 3C:
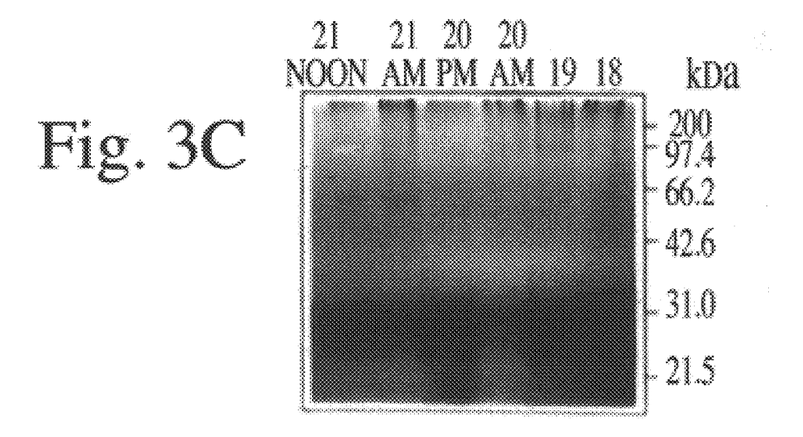
FIG. 3C is an image depicting a 1% casein zymographic analysis of homogenized fetal membranes obtained from pregnant Sprague-Dawley rats killed at the indicated days of pregnancy and times during normal gestation.

Demonstration of a Correlation between MMP-9 Activity and Fetal Membrane Rupture in Rats Experiments were carried out to determine the extent of MMP-9 activity in pregnant rats. Amnions were collected from pregnant Sprague Dawley rats killed at days 18, 19, 20 (a.m.), 20 (p.m.), 21 (a.m.) and 21 (noon) during normal gestation. Delivery normally occurred on the late afternoon of day 21. The amnionic membranes were homogenized and equal amounts of protein (16 microgram/lane) were subjected to polyacrylamide electrophoresis in gels impregnated with 1% gelatin (FIGS. 3A and 3B) or 1% casein (FIG. 3C) for zymography. MMP-2, detected as a lysis zone around 68 kDa, was present in amnions collected on days 18–21 (FIG. 3A). In contrast, MMP-9, detected as both a 92 kDa lysis zone and a dimer at 180 kDa, was present only on day 21 (FIG. 3A). Both MMP-2 and MMP-9 activities were not detected in the gels incubated in the presence of 10 mM EDTA (FIG. 3B). Caseinolytic activity characteristic of MMP-9 was also detected only on day 21 at a molecular weight of 92 kDa (FIG. 3C).

In conjunction with the appearance of MMP-9 activity beginning at about day 21, structural changes became apparent in the amnion at both the light and electron microscopic levels. These changes include a loss of collagen (observed as fibrils at the electron microscopic level) and proteoglycans, and necrosis of amnion epithelial cells was also observed during ultrastructural analysis. These changes some of which were observed by staining with Alcian blue and Periodic-Acid Schiff stain) resulted in alterations in the consistency of the amnion such that it became a fragile and viscous liquid-like.

These results demonstrated that MMP-9 activity was detectable in amnion only from about 12 to about 18 hours before delivery. MMP-2 activity, on the other hand, appeared to be constitutively expressed in the tissue. MMP-3 activity was not detectable in either gelatinolytic or caseinolytic assays. Since amnion structure changed dramatically on day 21 as determined by loss of collagen fibrils and proteoglycans observed by light and electron microscopy, these data suggested that MMP-9 was responsible for the changes in amnion structure that precede membrane rupture.

MMP-1 and MMP-3 have previously been identified in cultured cells derived from fetal membranes. However, the data illustrated in FIGS. 3A–3C clearly indicated that the presence or levels of these two matrix metalloproteinases were not correlated with structural changes in fetal membranes in the rat model. Nor were these enzymes detected in getalinolytic or caseinolytic assays in human female membranes in association with labor. On the basis of these data, there appeared to be no direct correlation between the presence of other known MMPs (other than MMP-9) and the process of fetal membrane rupture.

Example 4

Quantitative Gelatin Zymography

A collection swab was placed into a 1.5 ml conical tipped tube containing 500 microliter of SDS-PAGE sample buffer as disclosed in Laemmli, (1970, Nature 227:680–684). After 5 minutes at room temperature, the swab was withdrawn and the eluted proteins (in 30 microliter of sample buffer) were subjected to SDS-PAGE, performed according to Laemmili using a mini-gel apparatus (Bio-Rad, Richmond, Calif.). Gels were prepared according to standard protocols except that pig skin gelatin (1 mg/ml) was copolymerized in the 8% running gel and samples were added under non-denaturating conditions. A series of standards consisting of purified human MMP-9 prepared as described by Okada et al. (supra), and molecular weight markers were also run on the gel. The samples were electrophoresed under constant current (10 mA). Gels were then washed in 2.5% Triton X-100 for 30 minutes and were then incubated for 24 hours at 37° C. in 50 mM Tris Buffer, pH 7.4, containing 0.15 M NaCl and 30 mM $CaCl_2$. Gels were stained with Coomasie R-250 and zones of lysis of the gelatin were visualized following destaining of the gels. The gels were analyzed with a Resource Technology (Nashville, Tenn.) image analyzer to determine the extent of gelatin lysis. A standard curve was constructed from the lysis zones of the pure MMP-9 standards.

Example 5

Western Blot Analysis of MMP-9

Samples were prepared for SDS-PAGE as described above. The samples, each containing 30 microliters comprised the test sample, purified MMP-9 standards and molecular weight markers, were applied to 8% polyacrylamide gels and were electrophoresed under nonreducing conditions as described above. After electrophoresis, the separated proteins were transferred to a nitrocellulose membrane by eletrophoresis at 30 V for 12 hours at 4° C. as described by Towbin et al. (supra). A monoclonal antibody, 6-6B, directed against MMP-9 (Ramos-DeSimone et al. supra). that recognized both the pro-MMP-9 (92 kDa) and the active form of the enzyme (83 kDa) under non-reducing conditions, was incubated with the membrane at a concentration of 1 µg/ml overnight at 4° C. Binding of the primary antibody to the blot was detected using the Amersham ECL reagent system. The resulting X-ray film was analyzed densitometrically to quantitate MMP-9 forms in the sample using a standard curve generated with the MMP-9 standards.

Example 6

Sandwich Immunoassay of MMP-9

To elute proteins contained in the collection swab the collection swab was placed into a 1.5 ml conical tipped tube containing 500 microliter of phosphate buffered saline performed in 1% bovine serum albumin and 0.1% Triton X-100. The immunoassay was performed in microliter plates coated with an affinity-purified polyclonal antibody raised against a synthetic peptide representing the non-conserved metal binding domain of MMP-9. Aliquots of the sample and a standard curve of purified MMP-9 were applied to the plates. The plates were then incubated for 1 hour at 37° C. The plates were then washed with phosphate buffered saline containing –1% albumin and 0.1% Triton X-100. The monoclonal antibody, 6-63, which was radiolabeled with $^{125}I$ using the Bolton-Hunter reagent (10,000 cpm, 1 µg/ml), was then added in a 200 µl volume and the plates were incubated for 1 hour at room temperature. Unbound radiolabeled 6-6B antibody was washed from the wells using phosphate buffered saline containing 1% bovine serum albumin and –0.1% Triton X-100 by washing three times in a volume of 500 μl each. The radioactivity bound to the microliter plates was then measured in a gamma counter. A standard curve was constructed by subtracting a blank value (wells to which no sample or standard were added) from those generated using standard concentrations of MMP-9 (i.e., the standard curve). The amount of MMP-9 in the samples was assessed by interpolation using the standard curve.

Example 7

Transfection of Amnion Cells Grown on a Matrix Containing Type IV Collagen with MMP-9 Induces Anoikis and Apoptosis To test the hypothesis that induction of type IV collagenase activity causes type IV collagen degradation, cell detachment and subsequent cell death, human amnion epithelial cells (WISH cells) were cultured in defined medium on a matrix consisting of type I and type IV collagen.

Human amnion epithelial cells (WISH cells) were obtained from the American Tissue Type Collection (Rockville, Md.). Cells were cultured in serum-free Kennett's HY medium containing 1% bovine serum albumin on glass coverslips coated with a substrate of rat tail type I collagen (Collaborative Research) and mouse type IV collagen derived from Engelbreth-Holm-Swarm lathrytic tumor (Collaborative Research). At 60% confluence, the cells were transfected with a plasmid expressing human pro-MMP-9 in pCMV5 created by cloning the human pro-MMP-9 cDNA (Wilhelm et al., 1989, J. Biol. Chem. 264(29):17213–17221) into the pCMV5 vector (Andersson et al., 1989, J. Biol. Chem. 264:8222–8229), or an empty plasmid vector using Lipofectamine. In some experiments, batimistat (BB-94, British Biotech), was added to the medium in dimethyl sulfoxide (DMSO) at a concentration of 100 μM. Control cultures were treated with the DMSO vehicle. After approximately 30–48 hours, when detachment of the MMP-9 transfected cells from the coverslips was first noted, the medium was collected for zymography and the cells were fixed for analysis of apoptosis using an immunohistochemical method to detect nuclear DNA cleavage (Lei et al., 1997, J. Clin. Invest. 98:1971–1978). Cell detachment in the MMP-9-expressing WISH cells was extensive if incubation of cultures was continued beyond 48 hours after transfection, whereas cells transfected with control plasmid remained attached. Cells in five randomly selected fields on each coverslip were scored for nuclear DNA fragmentation to determine the percentage of cells undergoing apoptosis. The significance of differences between treatment groups was assessed by Student's t test.

Transfection of the WISH cells with a plasmid expressing human pro-MMP-9 increased the production of the 92 kDa type IV collagenase as detected by zymographic analysis of the culture medium. Although not detectable in the culture medium by zymography, activated MMP-9 is presumably generated from the pro-enzyme. Transfection with the pro-MMP-9 expression plasmid also caused cell detachment and increased intranucleosomal DNA cleavage, a feature of apoptosis, as assessed by immunohistochemical detection of 3'-end labeled nuclear DNA fragments. The percentage of cells undergoing apoptosis was increased from an average of 34% to 45% ($P<0.02$). The MMP inhibitor, batimistat added at a concentration of 100 μM, completely blocked the effects of MMP-9 expression on apoptosis (Table 1).

TABLE 1

| Treatment | % Apoptotic Cells | |
|---|---|---|
| | Expt. 1 | Expt. 2 |
| pCMV5 + DMSO | 4.3 | 2.0 |
| pCMV5 + batimastat | 11.6 | 3.0 |
| pCMV5-MMP-9 + DMSO | 67.0 | 27.6 |
| pCMV5-MMP-9 + batimastat | 8.4 | 2.6 |

WISH cells were transfected with the indicated plasmids. Cultures were treated with either batimastat (100 μM) or the DMSO vehicle. Apoptosis was quantitated as described in the text approximately 36 hours after transfection. Values are the means obtained from two experiments.

Example 8

Embryonic Membrane Morphological Changes

Amniotic membranes surrounding chicken embryos were examined for morphological changes during development, which changes were then correlated with the appearance of metalloproteinase activity. The effect of batimistat on the morphology and metalloproteinase activity was also examined.

Figure 4A:
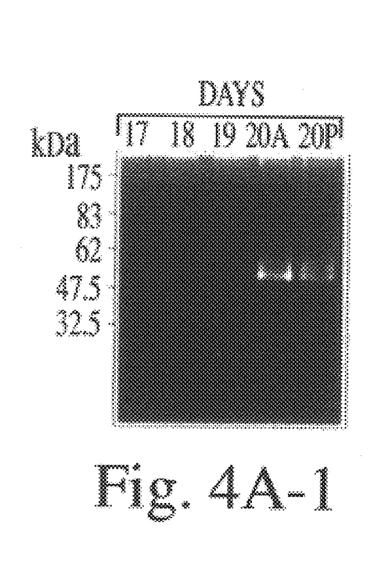
Figure 4A:
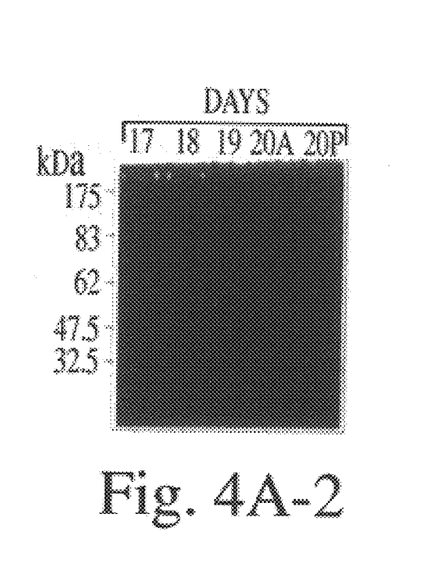
Figure 4A:
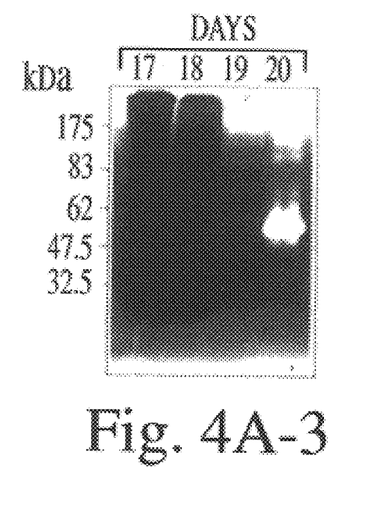
Figure 4A:
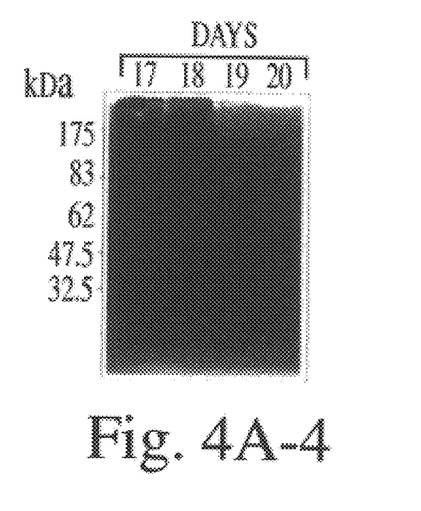
Figure 4B:
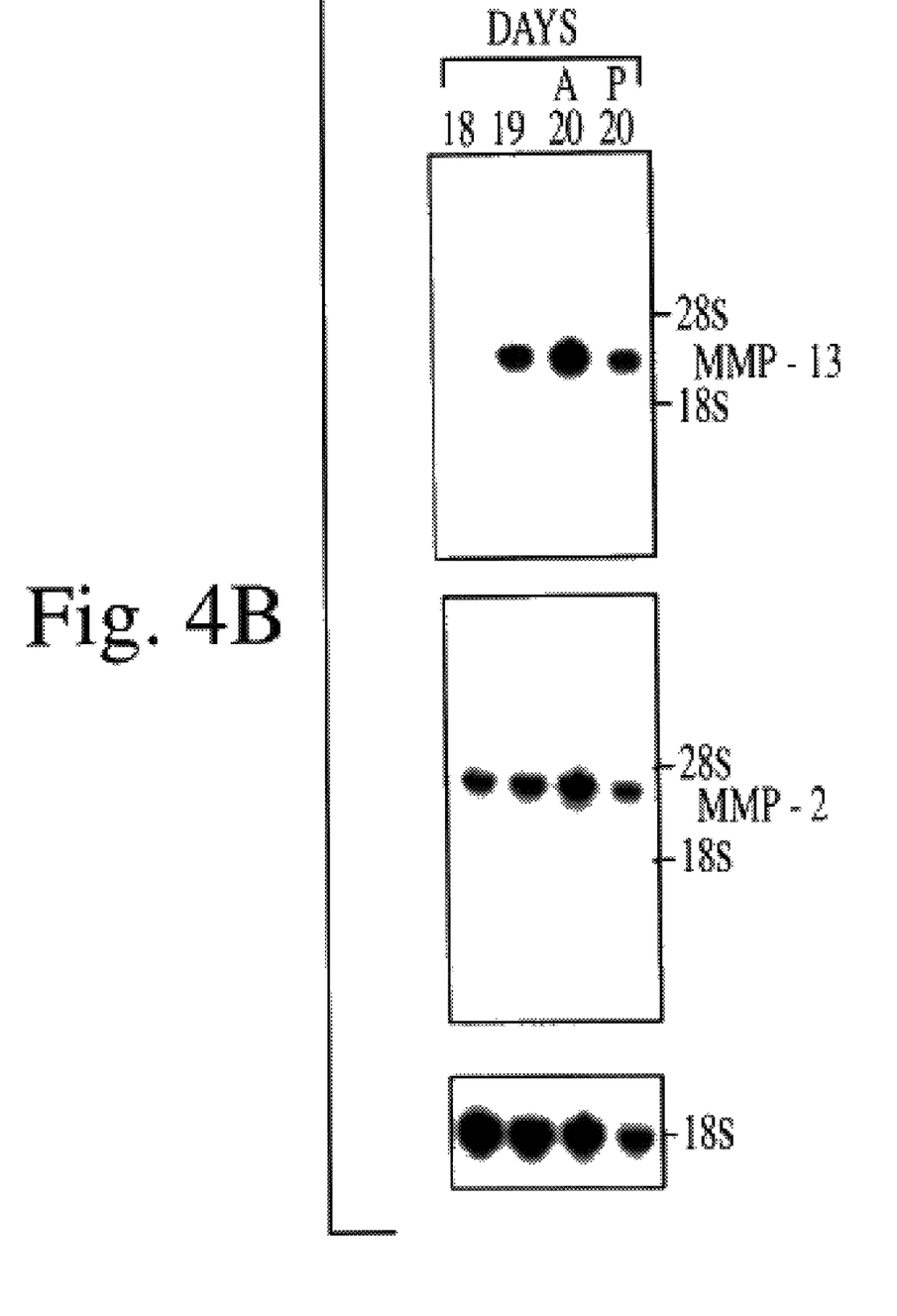
FIG. 4B is an image of a Northern blot depicting the expression of MMP-2-specific and MMP-13-specific mRNA.

The membranes surrounding the chicken embryo underwent striking morphological changes prior to hatching on embryonic Day 20, including loss of collagen and death of cells associated with the membranes. These changes in the structure of the membranes were associated with the induction of a matrix metalloproteinase homologous to MMP-13 which appeared in the membranes and the amniotic fluid. The appearance of MMP-13 activity was denoted by the 55 kDa band in zymograms of Day 20 (FIG. 4A) and the appearance of a 2.9 kb mRNA species in fetal membranes on Day 19. In contrast to the induction of MMP-13 activity, mRNA specific for MMP-2 was constitutively expressed in the membranes (FIG. 4B). This sequence of events was identical to changes observed in rat and human fetal membranes before the onset of active labor.

Figure 5A:
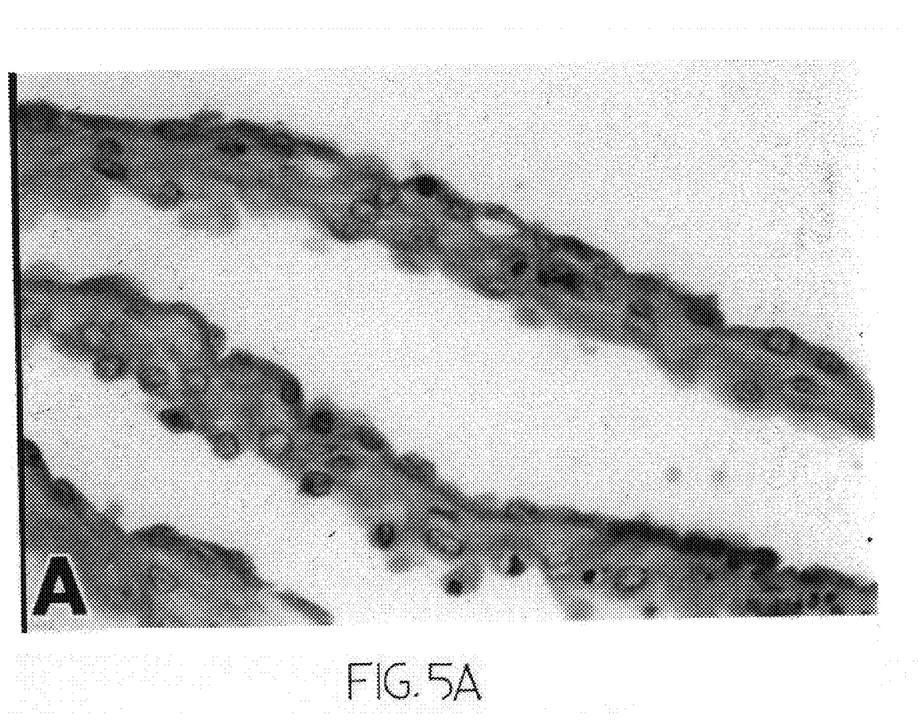
FIG. 5A depicts the structural changes observed by histological examination in the embryonic membranes after a daily injection of Batimistat in dimethylsulfoxide (DMSO).
Figure 5B:
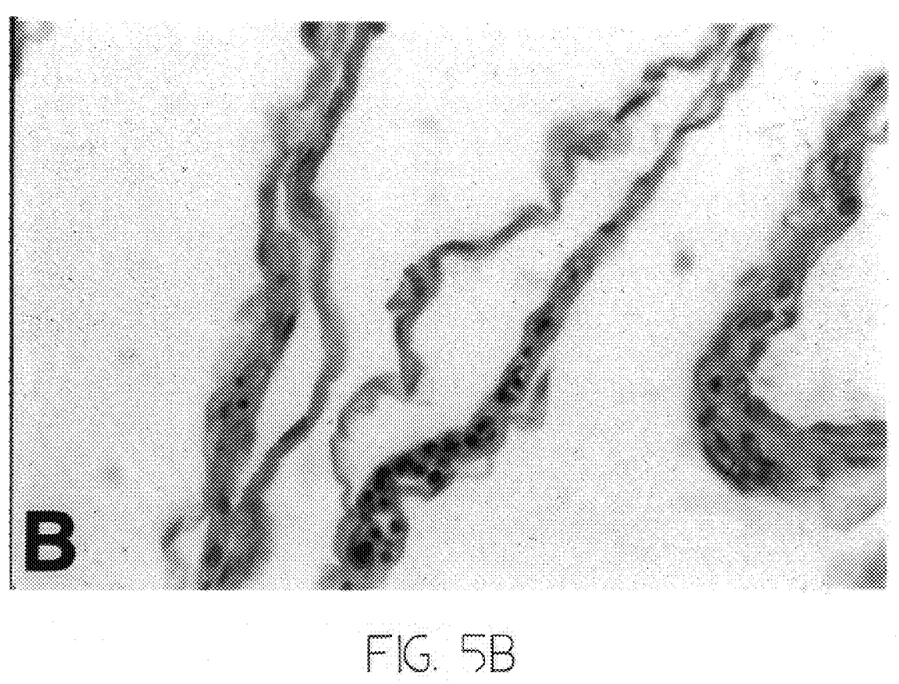
FIG. 5B is an image of a histological section of an embryonic membrane injected with the DMSO solvent.

Daily injection of 40 mg/kg batimistat in 100 microliter dimethylsulfoxide (DMSO) using a 22-gauge needle into the amniotic cavity of the chick embryos, starting on embryonic Day 17, prevented the structural changes observed in the membranes on embryonic Day 20 (FIG. 5A). Injection of DMSO in the absence of batimistat did not prevent the dissolution of the membranes by embryonic Day 20 (FIG. 5B). These results establish that batimistat has an effect on membrane alterations which occur during the onset of labor.

Example 9

The Effect of Recombinant Human TIMP-1 on Rat Fetal Membranes

The effect of recombinant human TIMP-1 on rat fetal membrane was examined in the experiment described below.

Recombinant human TIMP-1 (50 micrograms) produced by bacterial expression (Oncogene Research Products) was injected into the sacs of three rat fetuses of one horn and a control saline vehicle was injected into sacs in the contralateral horn in the same rats on Day 18 of pregnancy. The animals were killed on the morning of Day 21, amniotic membranes were obtained and were examined morphologically. The results of this study are presented in FIG. 6. FIG.

Figure 6A:
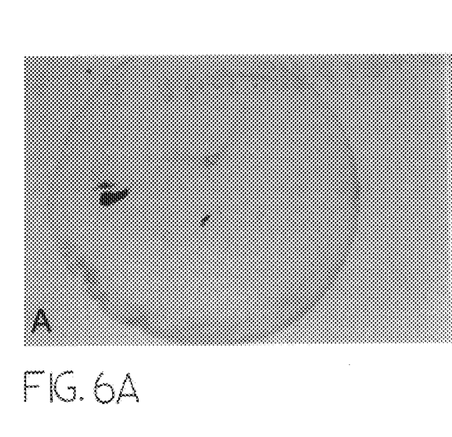
FIGS. 6A and 6B is a pair of images depicting the effect of recombinant human TIMP-1 on rat fetal membranes.
Figure 6B:
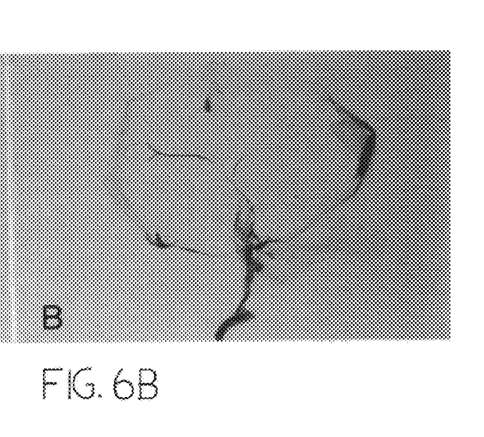

6, lane A represents the control membrane. In this membrane, it is evident that the yolk sac placenta had thinned and lost vascularity and the amnion is a gel. FIG. 6, lane B represents TIMP-1 treated membrane. The integrity of the yolk sac placenta and its vasculature as well as the amnion (arrow) were maintained.

The disclosure of publications and patent applications cited herein are herein incorporated by reference.

While this invention has been disclosed with reference to specific embodiments, it is apparent that other embodiments and variations of the invention may be devised by others skilled in the art without departing from the true spirit and scope of the invention. The appended claims are intended to be construed to include all such embodiments and equivalent variations.

What is claimed is:

1. A method of delaying the onset of fetal membrane rupture in a human comprising administering to said human a matrix metalloproteinase-9 inhibitor in an amount effective to delay the onset of fetal membrane rupture in said human, wherein said matrix metalloproteinase-9 inhibitor is a hydroxamic acid-based compound.

2. The method of claim 1, wherein said matrix metalloproteinase-9 inhibitor is suspended in a pharmaceutically acceptable carrier.

3. The method of claim 2, wherein said matrix metalloproteinase-9 inhibitor is administered to said human by a route selected from the group consisting of intra-amniotic, vaginal and parenterally.

4. The method of claim 2, wherein said matrix metalloproteinase-9 inhibitor is administered to said human in a dosage of from at least about 0.1 mg/kg of body weight per day to about 300 mg/kg of body weight per day.

5. The method of claim 4, wherein said dosage is from at least about 1 mg/kg of body weight per day to about 250 mg/kg of body weight per day.

6. The method of claim 5, wherein said dosage is from at least about 25 mg/kg body weight per day to about 250 mg/kg of body weight per day.

7. The method of claim 1, wherein said matrix metalloproteinase-9 inhibitor is a hydroxamic acid-based compound having either Formula I or Formula II or a salt thereof, wherein Formula I has the structure:

and Formula II has the structure:

wherein $R^1$ represents a $C_1$–$C_6$ alkyl, phenyl, thiophenyl, substituted phenyl, phenyl ($C_1$–$C_6$) alkyl, heterocyclyl, ($C_1$–$C_6$) alkylcarbonyl, phenacyl or substituted phenacyl group;

$R^2$ represents a hydrogen atom or a $C_1$–$C_6$ alkyl, $C_1$–$C_6$ alkenyl, phenyl ($C_1$–$C_6$) alkyl, cycloalkyl ($C_1$–$C_6$) alkyl or cycloalkenyl ($C_1$–$C_6$) alkyl group;

$R^3$ represents an amino acid side chain or a $C_1$–$C_6$ alkyl, benzyl, ($C_1$–$C_6$ alkoxy) benzyl, benzyloxy ($C_1$–$C_6$ alkyl) or benzyloxybenzyl group;

$R^4$ represents a hydrogen atom or a $C_1$–$C_6$ alkyl group;

$R^5$ represents a hydrogen atom or a methyl group;

n is an integer having the value 0, 1 or 2;

A in Formula I represents a $C_1$–$C_6$ hydrocarbon chain optionally substituted with one or more $C_1$–$C_6$ alkyl, phenyl or substituted phenyl groups; and A in Formula II represents a hydroxyl (OH) group or a sulfhydryl group (SH) wherein said sulfhydryl group is capable of forming a disulfide linkage to another monomer of Formula II.

8. The method of claim 7, wherein said matrix metalloproteinase-9 inhibitor is batimastat.

* * * * *